(12) United States Patent
Ericson

(10) Patent No.: US 11,383,002 B2
(45) Date of Patent: *Jul. 12, 2022

(54) PLASMA-BASED FILMS AND METHODS FOR MAKING AND USING THE SAME

(71) Applicant: OCTAPHARMA AG, Lachen (CH)

(72) Inventor: Daniel Grant Ericson, Rochester, MN (US)

(73) Assignee: OCTAPHARMA AG, Lachen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/032,331

(22) Filed: Sep. 25, 2020

(65) Prior Publication Data
US 2021/0008243 A1 Jan. 14, 2021

Related U.S. Application Data

(63) Continuation of application No. 16/305,168, filed as application No. PCT/US2017/035159 on May 31, 2017.

(60) Provisional application No. 62/343,840, filed on May 31, 2016.

(51) Int. Cl.
*A61L 15/40* (2006.01)
*A61L 31/00* (2006.01)

(52) U.S. Cl.
CPC .............. *A61L 15/40* (2013.01); *A61L 31/005* (2013.01); *A61L 2400/04* (2013.01)

(58) Field of Classification Search
CPC ...... A61L 15/40; A61L 31/005; A61L 2400/04
See application file for complete search history.

(56) References Cited

U.S. PATENT DOCUMENTS

| 8,529,959 | B2 | 9/2013 | Campbell et al. | |
| 2004/0147024 | A1* | 7/2004 | Crowe | A61K 47/6901 435/455 |
| 2007/0275461 | A1* | 11/2007 | Jorcano Noval | C12N 5/0698 435/371 |
| 2011/0318404 | A1* | 12/2011 | Kushnir | A61K 35/14 424/445 |
| 2015/0351754 | A1* | 12/2015 | Harris | A61B 17/07207 606/219 |

FOREIGN PATENT DOCUMENTS

| EP | 0 341 007 | 11/1989 |
| EP | 0 485 210 | 5/1992 |
| WO | 03/035115 | 5/2003 |

OTHER PUBLICATIONS

Google search citing Cambridge Dictionary definition of "tight turn." Nov. 4, 2020.*
P.J. Gaffney and T.A. Edgell, Thromb Haemost. Sep. 1995; 74(3); 900-3 (Year: 1995).*
International Search Report and Written Opinion of the International Searching Authority, dated Dec. 22, 2017 in corresponding International Patent Application No. PCT/US2017/035159.

* cited by examiner

*Primary Examiner* — Hasan S Ahmed
(74) *Attorney, Agent, or Firm* — Wenderoth, Lind & Ponack, L.L.P.

(57) ABSTRACT

The present invention relates to plasma-based films and in particular to flexible plasma-based films. The invention further relates to and to methods of making and using the flexible plasma-based films. Embodiments of the invention have been particularly developed for making flexible plasma-based films useful as a hemostat in the treatment and/or prevention of mild to severe as well as arterial bleedings, as an anti-adhesive sheet to reduce or prevent development of surgery-induced adhesions, as a wound healing patch, as a wound dressing, or as a film useful in hernia repair. Embodiments of the invention will be described hereinafter with reference to these applications. However, it will be appreciated that the invention is not limited to this particular field of use.

15 Claims, 4 Drawing Sheets

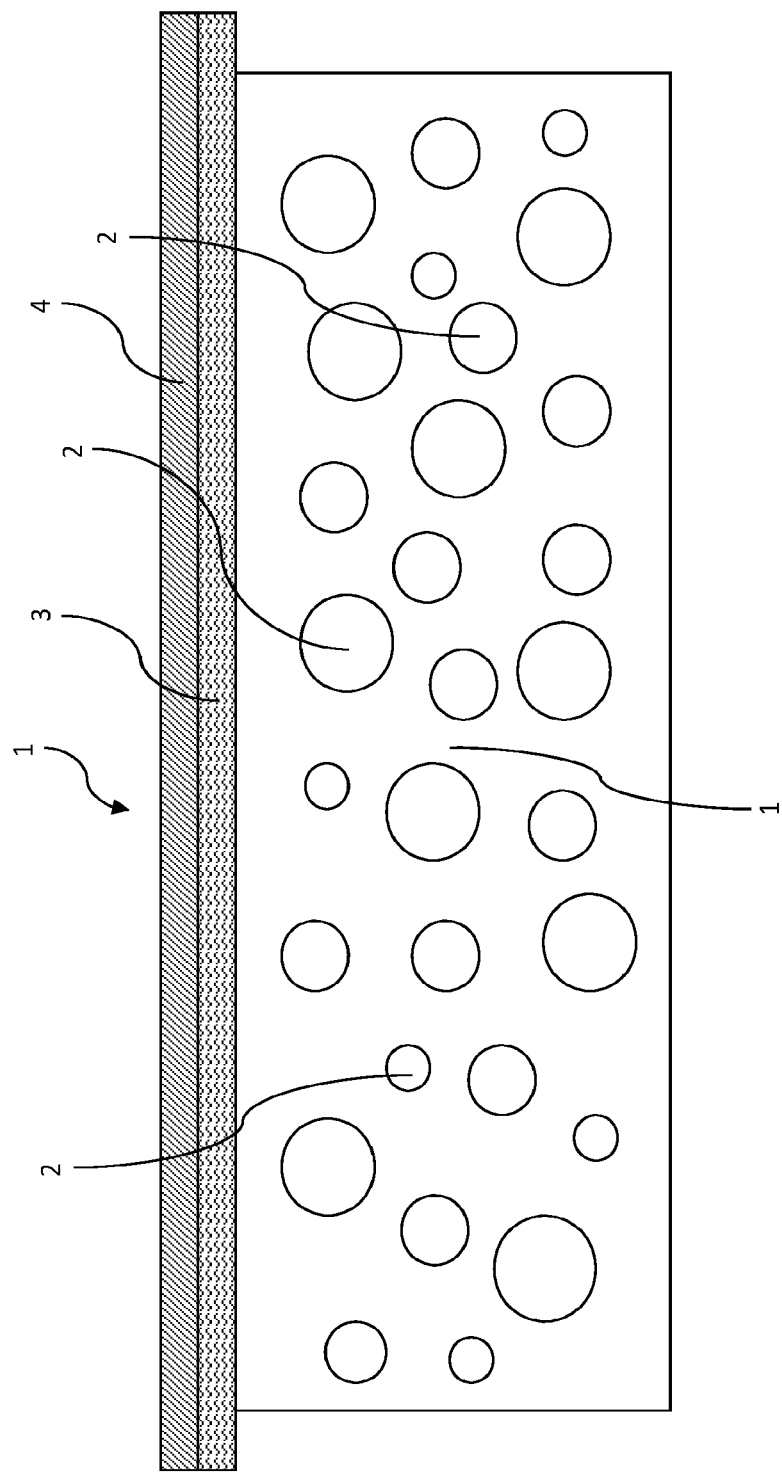

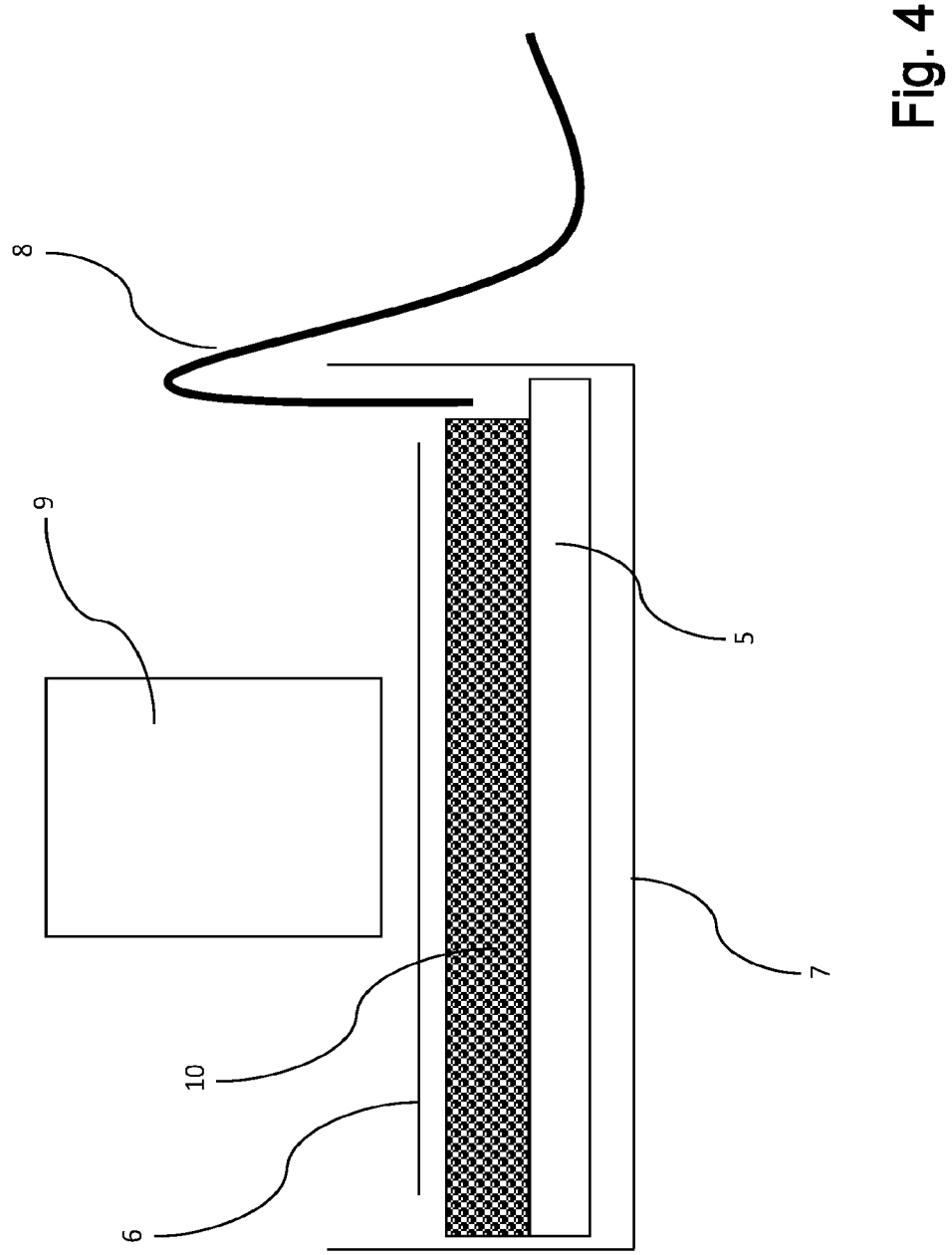

PLASMA-BASED FILMS AND METHODS FOR MAKING AND USING THE SAME

FIELD OF THE INVENTION

Figure 1:
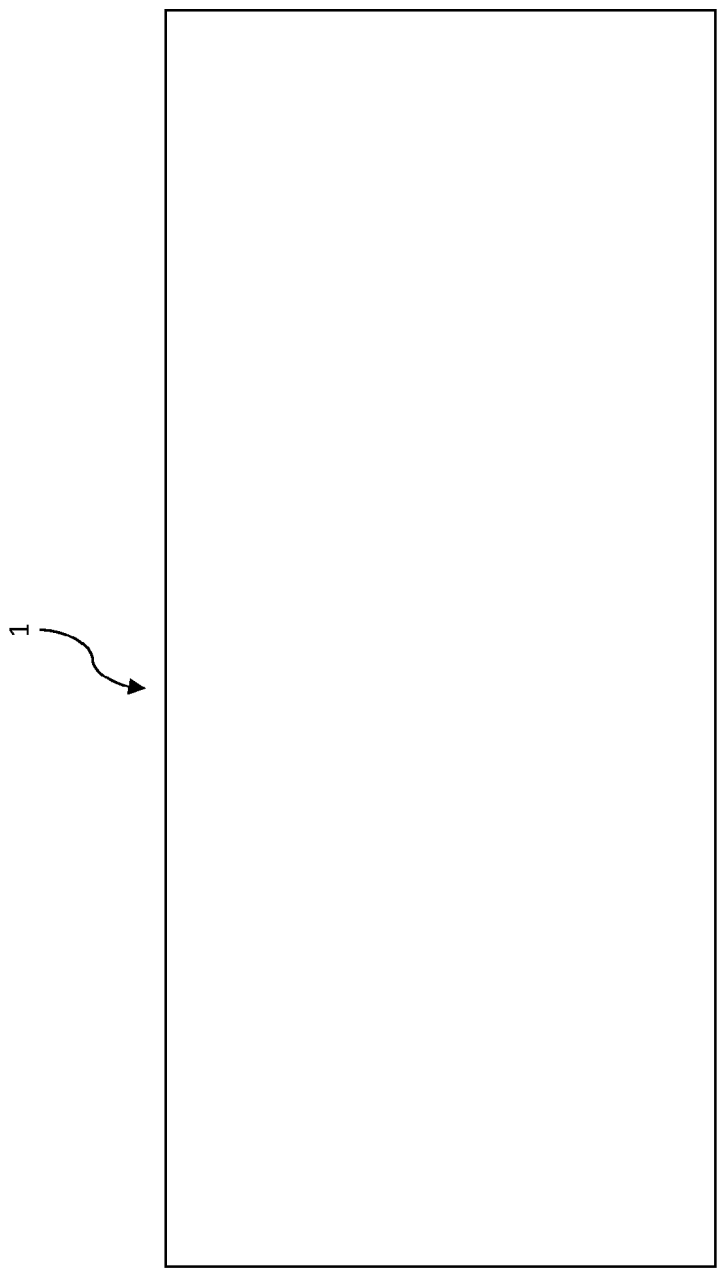

The present invention relates to plasma-based films and in particular to flexible plasma-based films. The invention further relates to methods of making and using the flexible plasma-based films.

Embodiments of the invention have been particularly developed for making flexible plasma-based films useful as a hemostat in the treatment and/or prevention of mild to severe as well as arterial bleedings, as an anti-adhesive sheet to reduce or prevent development of surgery-induced adhesions, as a wound healing patch, as a wound dressing, or as a film useful in hernia repair. Embodiments of the invention will be described hereinafter with reference to these applications. However, it will be appreciated that the invention is not limited to this particular field of use.

BACKGROUND OF THE INVENTION

Any discussion of the background art throughout the specification should in no way be considered as an admission that such art is widely known or forms part of common general knowledge in the field.

Films or sheets for use as medical products often contain embedded material such as fibers or fabrics to alter/improve the mechanical properties of such films or sheets, in particular to improve their resistance to pressure. However, depending on the kind of fibers and/or fabrics used, such enforced films or sheets are known to trigger complications in situ due to only partial biodegradability of the fibers and fabrics. Typical complications arising include the development of connective tissue between otherwise unrelated tissues and/or organs leading to post-surgical/surgery-induced adhesions Post-surgical/surgery-induced adhesions can lead to severe clinical complications such as loss of sensation, infertility, intestinal blockage and pelvic pain. The severity of the symptoms depends on the location and size of the adhesion. The number of patients suffering from post-surgical/surgery-induced adhesions is increasing and 55%-90% of patients that undergo gynecological and/or abdominal surgeries face complications arising from adhesions.

Entirely biodegradable fibrin films are known and plasma-based films have been described, for example see EP 0485210 A2 and U.S. Pat. No. 8,529,959 B2. As already indicated above, plasma-based, topical or implantable medical products such as films or sheets generally have a biocompatibility advantage in comparison to similar films or sheets comprising non-plasma based materials such as fibers and/or fabrics. In addition to the complications described above, plasma-based products such as films are suitable to provide individual patients with an implantable, plasma-based product generated from their own plasma providing a very high degree of biocompatibility.

EP 0485210 A2 discloses a manufacturing method for blood plasma-based films comprising the clotting of 50 ml citrated plasma with 8-10 NIH units of thrombin in a mold apparatus. However, the blood plasma-based films prepared in accordance with the disclosure of EP 0485210 A2 are brittle, and therefore inflexible, and display only poor mechanical strength such that the films break upon folding, making them unsuitable for applications where flexibility and/or pressure resistance is required.

U.S. Pat. No. 8,529,959 B2 discloses sheets comprising a blood plasma-derived plastic. The blood plasma-derived plastic is described as being obtained by clotting of blood with calcium, drying the obtained clot and grinding of the dried clot to produce plasma clot powder, which is mixed with glycerol to prepare a dough comprising 65% plasma clot powder and 35% glycerol, and wherein the dough is subsequently pressure-molded at an elevated temperature and high pressure to form the sheets. The sheets prepared in accordance with the disclosure of U.S. Pat. No. 8,529,959 B2 have a very limited flexibility and poor mechanical strength such that the sheets break upon folding making them unsuitable for applications where flexibility and or pressure resistance is required.

Accordingly, a need for improved biodegradable, flexible plasma-based films or sheets exist in the field. In particular, plasma-based films or sheets having a high degree of flexibility as well as high mechanical strength are needed.

SUMMARY OF THE INVENTION

It is an object of the present invention to overcome or ameliorate at least one of the disadvantages of the prior art, or to provide a useful alternative. In particular, it is an object of the present invention to provide improved flexible, plasma-based films and to provide improved methods for making and using such films, for example in the treatment and/or prevention of medical indications.

The present invention is inter alia based on the surprising finding that the flexibility and/or elasticity and/or mechanical strength of plasma-based films, when expressed as a function of fold-number, fold endurance and/or as a function of a plasma-based film's resistance to burst pressure, can be improved by mixing blood plasma with thrombin and/or calcium in excess of the amount required to induce clotting of the plasma, wherein the plasma is contained within a mold of a desired volume and shape.

Accordingly, in a first aspect, the present invention relates to a method of making a flexible plasma-based film comprising the steps of:
  (a) mixing blood plasma with more than 2 International Units (IU) of thrombin per milliliter (ml) of the plasma and/or with about 0.65 to 1.3 mg of calcium ions per milliliter (ml) of the plasma to induce clotting of the plasma, wherein the plasma is contained within a mold; and
  (b) maintaining the plasma in the mold for the time required for the plasma to clot and to form the film, wherein optionally during or at the end of the time a pressure is applied to the plasma in the mold.

Furthermore, it was surprisingly found that the flexibility of plasma-based films can be improved by mixing blood plasma with at least one activator of the coagulation system in a mold, and applying pressure to the plasma in the mold during or at the end of the time required for the plasma to clot.

Accordingly, in a second aspect, the present invention relates to a method of making a flexible plasma-based film comprising the steps of:
  (a) mixing blood plasma with an activator of the coagulation system to induce clotting of the plasma, wherein the plasma is contained within a mold; and
  (b) maintaining the plasma in the mold for the time required for the plasma to clot and to form the film, wherein during or at the end of the time a pressure ranging from about 0.3 to 125 pounds per square inch (psi) is applied to the plasma in the mold to form the film.

In light of the above, it will be understood that the present invention, in one or more preferred embodiments, also relates to a method of making a flexible plasma-based film comprising the steps of:

(a) mixing blood plasma with about more than 2 International Units (IU) of thrombin per milliliter (ml) of the plasma and/or with about 0.65 to 1.3 mg of calcium ions per milliliter (ml) of the plasma to induce clotting of the plasma, wherein the plasma is contained within a mold; and (b) maintaining the plasma in the mold for the time required for the plasma to clot and to form the film, wherein during or at the end of the time a pressure ranging from about 0.3 to 125 pounds per square inch (psi) is applied to the plasma in the mold.

In the methods of the first and second aspects, as well as in embodiments where the specific method steps of the two first aspects are combined, the blood plasma is mixed with about 2.9 to 3.1 IU of thrombin per ml plasma to induce clotting in the mold and is subsequently maintained in the mold for the time required for the plasma to clot and to form the film, and a pressure ranging from about 40 to 45 psi is applied to the plasma in the mold for about 50 to 70 seconds during or at the end of the time required for the plasma to clot.

In a third aspect, the present invention relates to a flexible plasma-based film when prepared by the methods according to the first or second aspects.

In a fourth aspect, the present invention relates to a flexible plasma-based film comprising between 0.1 to 10 IU of thrombin per ml of plasma and having a thickness ranging from about 0.005 to 0.1 mm, wherein the flexible film is characterized by a fold number of at least 1, such as at least 2, such as at least 4, such as at least 5. Preferably, in the embodiments of the present invention the flexible plasma-based films can also be characterized: by a fold endurance of at least 10, such as at least 20, such as at least 30, such as at least 40, such as at least 50, such as at least 60, such as at least 70, such is at least 80, such as at least 90, such is at least 100; and/or by a burst pressure of about 50 to 1000 mm Hg, or of about 100 to 1000 mm Hg, or of about 100 to 800 mm Hg, or of about 100 to 600 mm Hg, or of about 100 to 500 mm Hg, or of about 100 to 450 mm Hg, or of about 140 mm Hg, or of about 150 mm Hg, or of about 175 mm Hg, or of about 200 mm Hg, or of about 225 mm Hg, or of about 250 mm Hg, or of about 275 mm Hg, or of about 300 mm Hg, or of about 325 mm Hg, or of about 350 mm Hg, or of about 375 mm Hg, or of about 400 mm Hg.

In a fifth aspect, the present invention relates to the flexible plasma-based films according to the third or fourth aspects for use as a hemostat, preferably as a hemostat to stop a mild to severe bleeding. Accordingly, in embodiments of the fifth aspect, the invention also relates to a method of stopping a mild to severe bleeding, comprising applying the flexible plasma-based film according to the third or fourth aspect as a hemostat.

In a sixth aspect, the present invention relates to the flexible plasma-based films according to the third or fourth aspects for use as a hemostat to stop an arterial bleeding. Accordingly, in embodiments of the sixth aspect, the invention also relates to a method of stopping an arterial bleeding, comprising applying the flexible plasma-based film according to the third or fourth aspect as a hemostat.

In a seventh aspect, the present invention relates to the flexible plasma-based films according to the third or fourth aspects for use as an anti-adhesive sheet to reduce or prevent development of a surgery-induced adhesion. Accordingly, in embodiments of the seventh aspect, the invention also relates to a method of reducing or preventing development of surgery-induced adhesions, comprising applying the flexible plasma-based film according to the third or fourth aspect as an anti-adhesive sheet.

In an eighth aspect, the present invention relates to the flexible plasma-based films according to the third or fourth aspects for use as a wound healing patch. Accordingly, in embodiments of the eighth aspect, the invention also relates to a method of treating a wound, comprising applying the flexible plasma-based film according to the third or fourth aspect as a wound healing patch.

In a ninth aspect, the present invention relates to the flexible plasma-based films according to the third or fourth aspects for use as a wound dressing. Accordingly, in embodiments of the ninth aspect, the invention also relates to a method of treating a wound, comprising applying the flexible plasma-based film according to the third or fourth aspect as a wound dressing.

In a tenth aspect, the present invention relates to the flexible plasma-based films according to the third or fourth aspects for use in hernia repair. Accordingly, in embodiments of the tenth aspect, the invention also relates to a method of treating a hernia, comprising applying the flexible plasma-based film according to the third or fourth aspect.

FIGURES

Embodiments of the invention will now be described, by way of example only, with reference to the accompanying drawings in which:

FIG. 1 schematically shows a flexible plasma-based film (1) according to an embodiment of the present invention.

Figure 2:
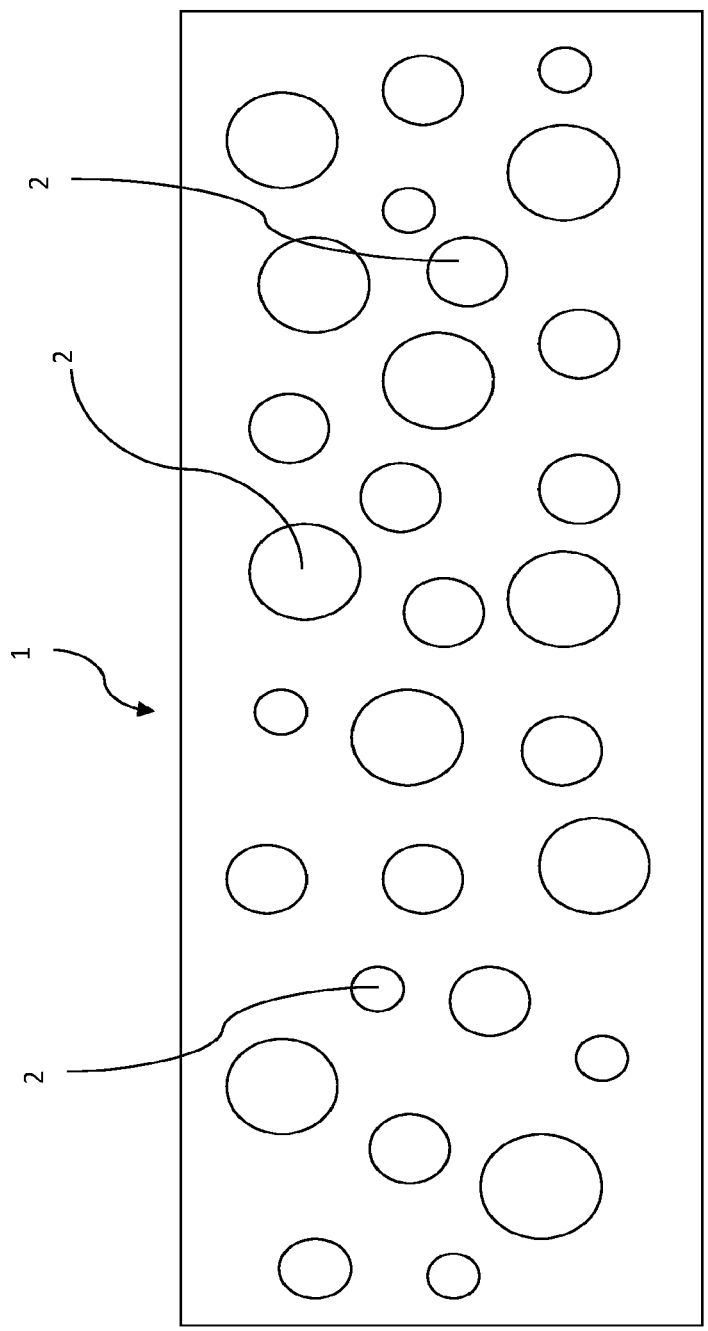

FIG. 2 schematically illustrates a plasma-based film (1) like the one shown in FIG. 1 comprising one or more pharmaceutically-active agents (2).

FIG. 3 schematically illustrates a plasma-based film (1) like the one shown in FIG. 1 comprising one or more pharmaceutically-active agents (2) embedded throughout the film to which two further pharmaceutically-active agents (3, 4) have been applied by subsequent spray-drying. In some embodiments the two further pharmaceutically-active agents may be spray-dried plasma (3) and a spray-dried activator of the coagulation system (4).

FIG. 4 schematically illustrates a vertical section through an apparatus suitable for making the plasma-based film of the present invention, where (5) is a downward-force piston, (6) is a non-porous plate for evenly applying pressure to the clotting/clotted plasma (not shown) in the mold (7) and comprising a liquid removal system of absorbent material (8) and vacuum-driven suction (9).

DETAILED DESCRIPTION OF THE INVENTION

In order to provide a clear and consistent understanding of the specification and claims, and of the scope to be given such terms, the following definitions are provided.

Definitions

In the context of the present application, the term "flexible" means that a structure such as a plasma-based film is capable of bending, even in tight turns, without breaking. In particular, a flexible film in the context of the present application is capable of folding without breaking and, as such, the film's degree of flexibility can be expressed by way of fold numbers or fold endurance as defined below. Further, a film's degree of flexibility can be expressed by the film's burst pressure also as defined below.

In the context of the present application, the term "plasma based", in general, means structures and materials such as the films according to the present invention, and in the case of multi-layered films the individual film layers, which are produced from blood plasma as the source material. In particular, if the majority of the components of such structures or materials is plasma, they are understood to be plasma-based structures or materials.

In the context of the present application, the term "film", in general means, thin, substantially planar, membranous structures, which can also be described as sheets. Notwithstanding, the term film in the context of the present application expressly encompasses single-layered films or sheets as well as composite multi-layered films or sheets. Further, a film in the context of the present application may comprise pharmaceutically-active agents either topically applied to the film, homogeneously distributed throughout the film or encapsulated between the film layers of a multi-layered film. The term "film" also encompasses structures having a degree of porosity that allows an uptake and/or release of substances such as pharmaceutically-active agents from the film. As such, the term "film" in the context of the present application also encompasses a thin, substantially planar, membranous scaffold upon which, or within which, pharmaceutically-active agents may be contained. Accordingly, the term film when used to describe embodiments of the present invention also encompasses plasma-based vessels or delivery devices for pharmaceutically-active agents comprised on or within the film.

In the context of the present application, the term "pharmaceutically-active agent" means a substance, particle and/or drug used to furnish pharmacological activity or to otherwise have a direct effect in the diagnosis, cure, mitigation, treatment or prevention of a medical indication, or to have a direct effect in restoring, correcting or modifying physiological functions.

In the context of the present application, the term "agent increasing the degree of cross linking between fibrin polymers" means agents that increase the number of links between the y- and a-chains of fibrin molecules thereby stabilizing fibrin fibers. Such agents, amongst others, include activated coagulation factor XIII (FXIIIa), calcium chloride, modified fibrin molecules such as mutated truncated fibrin molecules, and chain-specific antibodies.

In the context of the present application, the term "fold number" means the number of times a structure such as a plasma-based film can be bent in tight turns until the film disrupts. A simple test of determining fold number is described below.

In the context of the present application, the term "fold endurance" means the number of times a structure such as a plasma-based film can repeatedly be folded in a tight turn and again unfolded to its original position. Fold endurance in the context of the present application provides a means for wear resistance estimation of a flexible structure.

In the context of the present application, the term "burst pressure" means the maximum pressure a structure can withstand before breaking or disrupting. In the context of the present application the term burst pressure particularly means the maximum pressure a plasma-based film can withstand before breaking or disrupting.

In the context of the present application, the term "time required for plasma to clot" is given its plain-English meaning, i.e. it means the time required for the plasma used in the preparation of the plasma-based films described herein to clot.

In the context of the present application, the term "activator of the coagulation system" means substances, particles or agents that initiate coagulation/clotting. Such activators may initiate coagulation at any stage of the coagulation cascade and, as such, include agents acting on the intrinsic, extrinsic and common pathways of coagulation.

In the context of the present application, the term "hemostat" means devices suitable to reduce and ultimately stop bleeding. In particular, the term encompasses plasma-based films suitable to close blood vessels. As such, hemostats in the context of the present application include plasma-based films that can close blood vessels as a physical barrier, plasma-based films that can deliver hemostatic agents to the site of bleeding to close the blood vessel as well as combinations thereof.

In addition to the above definitions, and unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Further, reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

As used herein, the term "exemplary" is used in the sense of providing examples, as opposed to indicating quality. That is, an "exemplary embodiment" is an embodiment provided as an example, as opposed to necessarily being an embodiment of exemplary quality.

Flexible, Plasma-Based Films of the Invention and Methods for Making and Using the Same As described above, the flexibility, elasticity and/or mechanical strength of plasma-based films is important for such plasma-based films to be efficiently and successfully used as hemostats for stopping mild to severe bleedings and even for stopping arterial bleedings. In particular, the plasma-based films of the present invention provide the required flexibility, elasticity and mechanical strength required for the films to seal such bleeds, i.e. the flexibility necessary for the film to conform to the physiological topology of the site of the bleed and to withstand even arterial blood pressure at the site of the bleed.

Similarly, the flexibility, elasticity and mechanical strength of plasma-based films according to the present invention is important for such plasma-based films to be efficiently used as anti-adhesive sheets to reduce or prevent the development of surgery-induced adhesions.

Post-surgical/surgery-induced adhesions result from the formation of scar tissue following surgery. While adhesion is part of the normal healing response to tissue trauma, it can lead to severe post-surgical complications when a stable cross-connection between otherwise unconnected tissues arises as a result of adhesions.

In fact, more than 90% of patients develop peritoneal adhesions following abdominal or pelvic surgery. In most patients the adhesive tissue is subsequently remodeled and ultimately dissolved. However, in millions of patients adhesions form between organs and/or tissues that are normally separate, such as the intestines, bowels, uterus, ovaries and other organs, causing dysfunction and other possibly severe complications. For example, within the abdominal cavity adhesions can lead to small bowel obstruction, female infertility and pain. In addition, adhesions often make subsequent surgery more difficult and limit subsequent treatment options. For example, adhesions often impede subsequent minimally invasive surgery.

The plasma-based films of the present invention are suitable to provide anti-adhesion barrier sheets designed to act as a physical shield keeping damaged tissue separate from the surrounding tissue, thereby preventing undesirable adhesion. The plasma-based film when used as an anti-adhesive sheet separates the traumatized tissue during its initial time of healing but will ultimately break down entirely due to its biodegradation. In this respect, it is noteworthy that adhesion growth initiates within the first 3-5 days after surgery. As such, the plasma-based films of the present invention are particularly useful as anti-adhesive sheets allowing the separation of traumatized tissue from surrounding tissue during these first days of post-surgical healing, thereby reducing or preventing the development of surgery-induced adhesions and, ultimately, reducing or preventing at the risk of complications arising due to the formation of surgery-induced adhesions. As will be appreciated, the flexibility of the plasma-based films of the present invention provides a significant advantage when such films are used as anti-adhesive sheets due to their ability to conform to the physiological topology of the traumatized tissue thereby providing an efficient anti-adhesive barrier between the traumatized tissue and surrounding tissues.

Due to their biocompatibility and complete biodegradation over time, the flexible plasma-based films such as the film (1) schematically shown in FIG. 1 are also particularly suitable for use as wound dressings, wound healing patches, or for use in the repair of hernias or vascular lesions. In this regard, it is noteworthy that the plasma-based films of the present invention are typically non-toxic, non-interfering with normal healing, non-interfering with immunological functions, applicable in various settings such as bleeding, infections and anastomotic surgery and are, due to their flexibility, elasticity and high mechanical strength easy to handle and easy to apply.

Further, the plasma-based films of the present invention can serve as carriers, vessels and/or delivery devices for pharmaceutically-active agents, for example for agents useful in the treatment of the above-mentioned medical applications. For example, if the film is used as a wound healing patch, the film may carry one or more pharmaceutically-active wound healing agents, i.e. agents supporting wound healing. Alternatively, the films of the present invention may be used as bare wound dressings.

As such, the plasma-based films of the present invention such as the film (1) schematically illustrated in FIG. 2 may comprise at least one pharmaceutically-active agent (2). Preferably, the at least one pharmaceutically-active agent is selected from the group consisting of: antibiotic agents; anti-inflammatory agents; anti-infective agents; growth factors; chemokines; immunomodulators; wound healing agents; activators of the coagulation system; anti-coagulation agents; anti-adhesion agents; anti-fibrinolytic agents; penicillin; silver; chlorhexidine; cells; stromal cell-derived chemokines; stromal cell-derived factor 1 alpha; stromal cell-derived factor 1 beta; fibrinogen; Factor Vila; CXCL-12; heparin; aprotinin; tranexamic acid; non-ionic surfactants; Pluronic F68; TWEEN 80; COX-2 inhibitors; and Nimesulide.

The films of the present invention may be specifically engineered as delivery devices for the above-listed pharmaceutically-active agents. For example, a need exists for topically-applicable or implantable flexible plasma-based films, which may contain the pharmaceutically-active agents and/or deliver them to a treatment site.

Non-ionic surfactants, such as Polyoxyethylene sorbitan esters, in particular Polyoxyethylene (20) sorbitan monooleate (TWEEN-80®), Polyoxyethylene-polyoxypropylene block copolymers, in particular Pluronic F68®, or COX-2 inhibitors, in particular N-(4-Nitro-2-phenoxyphenyl)methanesulfonamide (Nimesulide®), or combinations thereof are particularly useful when plasma-based films for use as anti-adhesive sheets to reduce or prevent the development of surgery-induced adhesions are to be prepared. In such films, these agents may homogeneously be distributed throughout the film, or may be applied topically to the film, either alone or as a combination of agents.

In some embodiments the agent is homogenously distributed throughout the film. In other embodiments the agent is topically applied to the film. In yet further embodiments of the present invention, the plasma-based film may comprise a pharmaceutically-active agent homogenously distributed throughout the film and further comprise the same or another pharmaceutically-active agent topically applied to a surface of the film.

In embodiments where the agents are homogeneously distributed throughout the film, the agents become "trapped" within the film during formation of the plasma-based films due to clotting of the plasma. After implantation the plasma-based film will degrade (mainly due to lytic factors, hydration and mechanical wear) thereby successively releasing the pharmaceutically-active agents distributed throughout.

When an agent is topically applied to a film according to the invention, the agent can be applied by spray-coating, spray-drying, brushing and/or soaking.

Stromal cell derived chemokines are particularity interesting for use with films of the present invention. Stromal cell-derived factors 1-alpha and 1-beta are small cytokines that belong to the chemokine family, members of which activate leukocytes and are often induced in response to pro-inflammatory stimuli such as lipopolysaccharides, tumor necrosis factor (TNF) or interleukin-1 (IL1). Chemokines such as CXCL-12 inhibit the formation of connective tissue and are therefore useful agents for application to or distribution throughout films of the present invention when used as anti-adhesive sheets.

Once the films have been prepared, agents that inhibit further fibrin formation, such as heparin, aprotinin, tranexamic acid or other anti-fibrinolytics can also be added to plasma-based films to be used as anti-adhesive sheets, for example by topical application.

In some embodiments, the agent can be a single agent or can be a mixture of agents such as proteins, for example comprising a mixture of activators of the coagulation system such as plasma itself.

In some embodiments, the plasma-based films of the present invention may comprise more than one pharmaceutically-active agent homogenously distributed throughout the film and/or more than one pharmaceutically-active agent topically applied to the film.

In one or more preferred embodiments
(i) a first pharmaceutically-active agent is topically applied to the film, optionally by spray-drying,
(ii) a separation layer is subsequently applied onto the topically-applied first agent, and
(iii) a second pharmaceutically-active agent is topically applied onto the separation layer.

In such embodiments the first pharmaceutically-active agent may be fibrinogen, the separation layer may comprise starch, optionally gelatinized starch, and the second pharmaceutically-active agent may be thrombin. Preferably the fibrinogen is applied by spray-drying on a film layer, application of still-liquid gelatinized starch (prepared for example by gelatinizing 2.5 g of starch in 50 ml water by heating to 125° C.) on top of the fibrinogen layer and applying a pressure or about 15.5 psi (105 kPa) to the film. Typically, 2 ml of gelatinized starch are sufficient to cover a 4"×4" film with a separation layer. Subsequently, thrombin is applied onto the separation layer. Spray-drying of about 5 ml of a 300 IU/ml thrombin solution on a 4"×4" film proved to be most effective.

In alternative embodiments, the film of the present invention may comprise a topically applied pharmaceutically-active agent for use as a hemostat on just one outer surface of the layered film, while one of the inner layers comprises a different agent, for instance an antibiotic. The topically applied hemostatic agent on the film surface may be released and act immediately upon application of the film to a wound thereby providing an immediate beneficial hemostatic effect, while the antibiotic agent from the inner layer(s) of the film is only released after the immediate hemostatic effect, thereby providing an antibiotic effect during subsequent healing stages. As such, in such embodiments, topical application can provide for an immediate release effect of an agent, whereas homogeneous distribution throughout the film may allow for a retarded-release or slow-release effect of an agent.

In other embodiments, and referring to FIG. 3, the plasma-based film (1) optionally comprising a pharmaceutically active agent (2) homogeneously distributed throughout, can also be coated with spray-dried plasma (3) to provide a layer of plasma proteins to the outer surface of the film. Air gun spraying can be utilized for topical application of plasma as it maintains the plasma proteins' activity after drying. In effect this topical application by spray-drying provides a plasma-based film comprising active coagulation proteins on its outer surface. The activities of fibrinogen and FXa of the clotting system remain intact such that the film can be used as a hemostatic dressing with a spray dried layer of active coagulation proteins. In addition, a final layer of an activator of the coagulation system (4) such as a thrombin converter can be sprayed on top of the spray-dried plasma. For example, the thrombin converter may be selected from: tissue factor, recombinant tissue factor, thrombin, kaolin, diatomaceous earth, and activators of the coagulation system. The so modified plasma-based film can be used as a hemostat for mild, moderate or severe bleedings.

Further, a flexible plasma-based film according to the present invention may be a composite film comprising several plasma-based film layers, i.e. a multi-layered plasma-based film. In some multi-layered plasma-based films each individual film layer may comprise no, the same or different pharmaceutically-active agents.

The degree of cross-linking between fibrin polymers of the flexible plasma-based film influences the degradation speed of the film, wherein a high degree of cross-linking correlates with slow degradation, and wherein a low degree of cross-linking correlates with fast degradation. Accordingly, controlling the degree of cross-linking allows for the control of the rate or speed of degradation and therefore allows for the film to be customized according to its application.

For example, if the film is to be used as an anti-adhesive sheet, the film should degrade within one to two weeks of implantation. In contrast, films used for hernia repair should have a much slower degradation speed leading to an almost-permanent implant, preferably requiring several weeks to months or, in particular instances, even several months to years, before complete degradation of the film. In general, the degradation speed can be optimized to suit a film's particular function, i.e. to promote healing, provide mechanical stability for a rupture or lesion covered by the film, etc.

Similarly, the degree of cross-linking between fibrin polymers of the film influences the release time of a pharmaceutically-active agent homogeneously distributed within the film, wherein a high degree of cross-linking correlates with longer release times, and wherein a low degree of cross-linking correlates with shorter release times. Accordingly, controlling the degree of cross-linking allows for the control of the release rate of a pharmaceutically-active agent homogeneously distributed throughout the films of the present invention.

The combination of the different features of the films described herein, i.e. monolayer films, multilayer films, different agents either applied topically or distributed throughout the film, allow for the production of films tailor-made for specific applications and even individual patients.

The flexible plasma-based film of the present invention is typically prepared from liquid plasma, where the plasma may be human or animal plasma. For example, the plasma is Fresh Frozen Plasma (FFP) or is pathogen-safe plasma. FFP can be obtained from a blood bank. However, plasmas obtained from a professional plasma manufacturer such as CLS Behring, Baxter or Octapharma are typically preferred as they provide much higher pathogen safety due to pathogen removal and inactivation methods incorporated in their production processes. Plasmas from plasma manufacturers are usually pooled and pathogen-safe plasmas.

In embodiments where pathogen-safe plasma is used as the source material for the plasma-based films of the present invention, the plasma has preferably been subjected to viral inactivation treatment, has been pasteurized, has been radiated, and/or has been nano-filtered. Typically, the pathogen-safe plasma being used as source material for the films of the present invention has been subjected to solvent/detergent treatment (S/D treatment) to inactivate any viral pathogens possibly contained therein.

In one or more preferred embodiments, the plasma-based films of the present invention have a thickness ranging from about 0.005 to 0.1 mm, or from about 0.005 to 0.09 mm, or from about 0.0075 to 0.08 mm, or from about 0.01 to 0.08 mm, or from about 0.01 to 0.07 mm, or from about 0.015 to 0.065 mm, or from about 0.02 to 0.06 mm, or from about 0.02 to 0.055 mm, or from about 0.02 to 0.05 mm, or from about 0.02 to 0.04 mm, or from about 0.02 to 0.03 mm, or about 0.01 mm, or about 0.02 mm, or about 0.03 mm, or about 0.04 mm, or about 0.05 mm, or about 0.06 mm.

As already indicated above, the particularly advantageous flexibility, elasticity and mechanical strength of the flexible plasma-based films of the present invention can be expressed by way of fold numbers, fold endurance and burst pressure of the films.

A simple test to determine film flexibility is the evaluation of a film's fold number. Such determination is accomplished by folding one half of the film on top of the other half, turning the stack by 90° and again folding one half of the stack on top of the other and so on until the film breaks or rupture. Each folding without triggering film rupture increases the fold number by 1. This test is particularly useful for the assessment of a plasma-based film's ability to maintain its integrity when being bent in tight turns. The flexible plasma-based films of the present invention are typically characterized by a fold number of at least 1, such as at least 2, such as at least 3, such as at least 4, such as at least 5.

Another test to determine film flexibility is the evaluation of fold endurance. Such determination is accomplished by repeatedly folding one half of the film on top of the other half and unfolding to its original position. Fold endurance is expressed by the number of such folding/unfolding repeats and provides a means for wear resistance estimation. The flexible plasma-based films of the present invention are typically characterized by a fold endurance of at least 10, such as at least 20, such as at least 30, such as at least 40, such as at least 50, such as at least 60, such as at least 70, such is at least 80, such as at least 90, such as at least 100.

Still another method for determination of film flexibility is the determination of burst pressure according to the Standard Test Method for Burst Strength of Surgical Sealants (ASTM-F 2392-04). A film is fastened in a fixture according to ASTM-F 2392-04 and the fixture is connected to a pump with a pressure transducer being attached inline between the pump and the burst pressure fixture. Pumping a fluid into the system increases the pressure until the film bursts. Thus obtained burst pressure is indicated as [mm Hg]. The flexible plasma-based films of the present invention are typically characterized by a burst pressure of about 50 to 1000 mm Hg, or of about 100 to 1000 mm Hg, or of about 100 to 800 mm Hg, or of about 100 to 600 mm Hg, or of about 100 to 500 mm Hg, or of about 100 to 450 mm Hg, or of about 140 mm Hg, or of about 150 mm Hg, or of about 175 mm Hg, or of about 200 mm Hg, or of about 225 mm Hg, or of about 250 mm Hg, or of about 275 mm Hg, or of about 300 mm Hg, or of about 325 mm Hg, or of about 350 mm Hg, or of about 375 mm Hg, or of about 400 mm Hg.

In some preferred embodiments of the present invention a flexible plasma-based film characterized by a burst pressure of at least 130 to 240 mm Hg, when the dry film (with about 4% residual water) has a film thickness of 0.03 mm, in particular by a burst pressure of 170 to 240 mm Hg for a 0.03 mm film in dry condition, or 130 to 180 mm Hg for a 0.03 mm film (film thickness in dry condition) after soaking for 10 minutes in an aqueous solution containing 10% glycerol is provided.

In other preferred embodiments of the present invention a flexible plasma-based film characterized by a burst pressure of at least 190 to 450 mm Hg when the dry film (with about 4% residual water) has a film thickness of 0.05-0.06 mm, in particular by a burst pressure of 300 to 450 mm Hg for a 0.05-0.06 mm film in dry condition, or 190 to 400 mm Hg for a 0.05-0.06 mm film (film thickness in dry condition) after soaking for 10 minutes in an aqueous solution containing 10% glycerol is provided.

Tensile strength was determined according to the Standard Test Method for Strength Properties of Tissue Adhesives in Lap-Shear by Tension Loading (ASTM F2255-05) by measurement with an Instron Model 58R4505 Mechanical Test System using a 50 N (~10 #) loadcell and a crosshead speed of 1.0 inch per minute. The samples had dogbone shape with a narrow region of 0.25" and were placed in the instrument with rubber lined pneumatic grips with the pressure set at 20 psi. The obtained tensile strength is given as pound-force [lbf]. The flexible plasma-based films of the present invention are typically characterized by a tensile strength of at least 0.25 lbf (approximately 1.1 N), such as at least 0.5 lbf (approximately 2.2 N), such as at least 0.75 lbf (approximately 3.3 N), such as at least 1 lbf (approximately 4.4 N), such as at least 1.2 lbf (approximately 5.28 N), or by a tensile strength ranging from about 0.25 lbf (approximately 1.1 N) to 1.5 lbf (approximately 6.6 N), such as from about 0.5 lbf (approximately 2.2 N) to 1.5 lbf (approximately 6.6 N), such as from about 0.7 lbf (approximately 3.08 N) to 1.5 (approximately 6.6 N), such as from about 0.8 lbf (approximately 3.52 N) to 1.5 lbf (approximately 6.6 N), such as from about 0.9 lbf (approximately 3.96 N) to 1.5 lbf (approximately 6.6 N), such as from about 1 lbf (approximately 4.4 N) to 1.5 lbf (approximately 6.6 N).

In some preferred embodiments the flexible plasma-based film of the present invention comprises one or more humectants. In particular, the film may be coated with humectants such as glycerol, for instance by soaking in 10% glycerol for 10 to 15 minutes, to prevent the film from becoming brittle during storage. It is also possible to admix the humectant during clotting of the plasma when preparing the film. In such embodiments, admixing 1-2% of glycerol, based on the total weight of the clotting mixture, is typically sufficient to prevent films from becoming brittle during storage.

Alternatively, the film may be packaged or pouched in a humidity-controlled container after preparation to preserve the film's flexibility. The pouch or container may be a foil pouch or another sterilization container. Typically the plasma-based films of the present invention are sterilized, preferably by gamma sterilization, e-beam sterilization, and/or UV sterilization An adhesive backing can be applied to the film to provide additional adhesion of the film to the tissue if so desired. Notwithstanding, typically, the plasma-based films of the present invention without an adhesive backing adhere to the tissue they are applied to such that stay sutures were generally not required during in situ testing in animal studies.

As indicated above, it was surprisingly found that the flexible plasma-based films of the present invention having the above-described characteristics and features can advantageously be prepared by the methods of the first and second aspects of the present invention mentioned above, i.e. that the flexibility, elasticity, and mechanical strength of plasma-based films can be improved by the particular methods of preparation.

Namely, in the first aspect, the present invention relates to a method of making a flexible plasma-based film comprising the steps of:

(a) mixing blood plasma with more than 2 International Units (IU) of thrombin per milliliter (ml) of the plasma and/or with about 0.65 to 1.3 mg of calcium ions per milliliter (ml) of the plasma to induce clotting of the plasma, wherein the plasma is contained within a mold; and (b) maintaining the plasma in the mold for the time required for the plasma to clot and to form the film, wherein optionally during or at the end of the time a pressure is applied to the plasma in the mold.

Furthermore, it was surprisingly found that the flexibility of plasma-based films can be improved by mixing blood plasma with at least one activator of the coagulation system in a mold, and applying pressure to the plasma in the mold during or at the end of the time required for the plasma to clot. The mold preferably has a volume and shape suitable for the preparation of the films of the present invention.

As such, and in accordance with the second aspect, the present invention relates to a method of making a flexible plasma-based film comprising the steps of:

(a) mixing blood plasma with an activator of the coagulation system to induce clotting of the plasma, wherein the plasma is contained within a mold; and (b) maintaining the plasma in the mold for the time required for the plasma to clot, wherein during or at the end of the time a pressure ranging from about 0.3 to 125 pounds per square inch (psi) is applied to the plasma in the mold to form the film.

In one or more preferred embodiments, the pressure ranges from about 30 to 95 psi, or from 30 to 56 psi, or from 40 to 50 psi, or from 40 to 45 psi, or is 44 psi. Preferably, the pressure is applied for only a fraction of time required for the plasma to, such as for 30 to 120 seconds, such as for 45 to 85 seconds, such as for 50 to 70 seconds, such as for 60 seconds.

Typically, the thrombin in the method of the first aspect or the activator of the coagulation system in the method of the second aspect are present in excess, such that the time required for the plasma to clot is relatively short ranging from about 5 to 20 minutes from mixing of the thrombin or the activator of the coagulation system with the plasma, or from about 10 to 20 minutes, or from about 12 to 18 minutes. In some embodiments the time required for the plasma to clot is 15 minutes. Accordingly, in some embodiments the pressure is applied after about 5 to 20 minutes from mixing of the thrombin of the activator of the coagulation system with the plasma, or after about 10 to 20 minutes, or after about 12 to 18 minutes, or after about 15 minutes.

In this regard, it is noteworthy that induction of clotting can be achieved in some instances simply by recalcification of the plasma. Alternatively, clotting can be induced by the addition of agents that convert the fibrinogen in the plasma to fibrin such as thrombin and thrombin-like coagulation activators. In addition, the extrinsic pathway of the coagulation system can be activated to induce clotting of the plasma. Such extrinsic activators are phospholipids, phospholipids containing, phosphatidylserine and phosphatidylcholine, tissue factor, recombinant tissue factor such as Dade Innovin, diatomaceous earth, or other common extrinsic pathway activators.

Accordingly, in some embodiments of the methods of the second aspect, the activator of the coagulation system is preferably selected from one or more members of the group consisting of: thrombin and thrombin-like coagulation activators; calcium; fibrinogen-to-fibrin converters; phospholipids; phosphatidylcholine; tissue factor; diatomaceous earth; zeolithes; kaolin; Factor Vila; and Factor Xa. In some embodiments of the methods of the second aspect the activator of the coagulation system is thrombin and/or calcium.

In some embodiments of the methods of the first or second aspects, the plasma is mixed with about 0.1 to 10 International Units (IU) of thrombin per milliliter (ml) of the plasma and/or with about 0.65 to 1.3 mg of calcium ions per milliliter (ml) of the plasma. Preferably the plasma is mixed with about 0.1 to 7 IU of thrombin per ml of plasma, or with about 0.15 to 6 IU of thrombin per ml of plasma, or with about 1 to 5 IU of thrombin per ml of plasma, or with about 2 to 4 IU of thrombin per ml of plasma, or with about 2.5 to 3.5 IU of thrombin per ml of plasma, or with about 2.9 to 3.1 IU of thrombin per ml of plasma, or the plasma is mixed with more than 2 IU of thrombin per ml of plasma, such as more than 2.5 IU of thrombin per ml of plasma, such as more than 2.75 IU of thrombin per ml of plasma, such as more than 3 IU of thrombin per ml of plasma, such as more than 3.25 IU of thrombin per ml of plasma, such as more than 3.5 IU of thrombin per ml of plasma, such as more than 3.75 IU of thrombin per ml of plasma, such as more than 4 IU of thrombin per ml of plasma and/or with about 0.65 to 1.3 mg of calcium ions per milliliter (ml) of the plasma.

In some embodiments of the methods of the first or second aspects, the steps of mixing and maintaining the plasma are performed at a temperature range from room temperature to about 40° C., or from 36 to 38° C., or at 37° C.

In some further embodiments of the methods of the first or second aspects, the pressure is applied to the plasma within the mold via a plate to form the film, preferably the plate is pressed onto the plasma in the mold by a pneumatic press.

In some embodiments, the methods of the first or second aspects further comprise a step of:

(c) removing excess liquid from the mold.

During this further step, the excess liquid is typically extruded from the clotted or clotting plasma when the pressure is applied. Preferably the excess liquid is removed by way of a liquid removal system, optionally selected from: a suction system such as a vacuum-driven suction system; and a system comprising adsorbent materials such as absorbent cloths, towels, membranes or gels.

For example, and referring to FIG. 4, the pressure can be applied to the clotting mixture (5) via a solid, non-porous plate (6) being slightly smaller than the outer perimeter of the mold (7). The plate is then placed under a liquid removal system (8) that will remove the excess aqueous portion of the plasma-based film during compression. Once the aqueous removal system (8) is in place force is uniformly placed on the plate (6), for example by way of a downward-force piston (9) of a pneumatic press. The force on the plate pressing down on the clotting mixture in the mold can be very low, e.g. as low as 5 pounds, or the force can be high, e.g. 2000 pounds. During application of the pressure, the excess aqueous portion of the plasma-based film, which contains primarily blood serum and excess water, is extruded or "squished" so that the excess aqueous portion of the plasma-based film is displaced to the outer perimeter of the plate (6). During this displacement step the aqueous phase is removed by the liquid removal system (8) via a vacuum-driven suction and can also be collected via absorbent material (10). At the end of the compression, the "squished" film can be removed from the container as a flat, highly compressed, low water content, high strength film.

In some embodiments, the methods of the first or second aspects further comprise a step of:

(d) drying the plasma-based film.

During this further step, the film is typically dried at room temperature and/or under negative pressure conditions such as in a laminar flow unit or a vacuum unit, or at increased temperatures such as in an oven.

In some embodiments the film prepared further comprises at least one pharmaceutically-active agent, preferably the agent is homogeneously distributed throughout the film or is topically applied to the film and may be selected from the group consisting of: antibiotic agents; anti-inflammatory agents; anti-infective agents; growth factors; chemokines; immunomodulators; wound healing agents; activators of the coagulation system; anti-coagulation agents; anti-adhesion agents; anti-fibrinolytic agents; penicillin; silver; chlorhexidine; stromal cell-derived chemokines; stromal cell-derived factor 1 alpha; stromal cell-derived factor 1 beta; fibrinogen; Factor VIIa; CXCL-12; heparin; aprotinin; tranexamic acid; non-ionic surfactants; Pluronic F68; TWEEN 80; COX-2 inhibitors; and Nimesulide.

In some further embodiments of the methods of the first or second aspects, the at least one pharmaceutically-active agent is homogeneously distributed throughout the film. In such embodiments, the step of mixing the blood plasma with the thrombin and/or calcium or with the activator of the coagulation system also comprises mixing the plasma with the at least one pharmaceutically-active agent to provide a clotting mixture with the proviso that the agent cannot be an anti-coagulation agent. Typically, the at least one pharmaceutically-active agent may constitute up to 5% of the total weight of the clotting mixture, such as up to 2%, preferably between 1 and 2%.

In this regard, it is noteworthy that admixture of the agents up to 5% of the total weight of the clotting mixture did not compromise mechanical stability of films produced. As shown in more detail in the Examples below, addition of 1-2% of anti-adhesive agents was sufficient for the films to display no to very minor adhesions in an animal study. In the animal model for the development of adhesions, the anti-adhesive sheets of the present invention led to less than 25% of the initially applied wound surface being covered with adhesions, in particular they displayed 0-15% wound surface coverage. In contrast, the best-performing commercially-available anti-adhesion film tested in the same animal model for the development of adhesions led to a wound surface coverage of at least 40%.

In some further embodiments of the methods of the first or second aspects, the at least one pharmaceutically-active agent is topically applied to the film, optionally the agent can be applied by spray-coating, spray-drying, brushing and/or soaking. In some preferred embodiments, the agent can be a mixture of proteins comprising activators of the coagulation system such as plasma.

In some further embodiments of the methods of the first or second aspects, the film may comprise several film layers prepared by successively repeating the steps of the methods of the invention in the mold to form a multi-layered plasma-based film, wherein, optionally, each individual film layer may comprise no, the same or different pharmaceutically-active agents. Preferably, several pharmaceutically-active agents may be topically applied simultaneously or successively.

In some further embodiments of the methods of the first or second aspects, the step of mixing the blood plasma with the thrombin and/or calcium or with the activator of the coagulation system also comprises mixing the plasma with an agent increasing the degree of cross-linking between the fibrin polymers generated during clotting of the plasma, preferably the agent is calcium chloride.

The mixing with further calcium chloride leads to the formation of highly cross-linked plasma-based films which are resistant to degradation in 8M urea over days, to weeks, to months. As such, if the plasma-based film to be prepared is to be a more rapidly degrading film, calcium chloride should not be added. In the absence of calcium chloride the fibrin in the plasma-based film has a very low degree of cross-linking and is rapidly degradable. For example, a film with a low degree of cross-linking dissolves in 8M urea within about 4 hours. Notwithstanding the above, even if having a high degree of cross-linking, the films of the present invention are fully biodegradable.

The blood plasma suitable for use in the methods of the first and second aspect can be animal or human blood plasma. Typically the plasma is Fresh Frozen Plasma (FFP) or is pathogen-safe plasma. In methods where pathogen-safe plasma is used, the plasma has been subjected to viral inactivation treatment, preferably solvent/detergent treatment (S/D treatment), and/or has been pasteurized, and/or has been radiated, and/or has been nano-filtered.

In some embodiments, the plasma-based film of the present invention has a water content of about 3 to 6% by weight, or of about 4 to 5% by weight, or of about 4% by weight. Residual water content was determined by evaluation of the weight of the film prior to determination (total weight) and after drying in an oven at 105° C. to constant weight. The difference in weight represents the weight of residual water (prior to oven drying) and is given as % residual water, based on total weight prior to oven drying. Films of the present invention having a residual water content of about 4% are referred to as "dry" films in the Examples below, while such films after soaking for 10 minutes in an aqueous solution containing 10% glycerol are referred to as "soaked films".

The methods of the first and second aspects are suitable for making flexible, plasma-based films having a thickness ranging from about 0.005 to 0.1 mm, or from about 0.005 to 0.09 mm, or from about 0.0075 to 0.08 mm, or from about 0.01 to 0.08 mm, or from about 0.01 to 0.07 mm, or from about 0.015 to 0.065 mm, or from about 0.02 to 0.06 mm, or from about 0.02 to 0.055 mm, or from about 0.02 to 0.05 mm, or from about 0.02 to 0.04 mm, or from about 0.02 to 0.03 mm, or about 0.01 mm, or about 0.02 mm, or about 0.03 mm, or about 0.04 mm, or about 0.05 mm, or about 0.06 mm. Notwithstanding, films with other thicknesses are also derivable by simply up- or down-scaling the volumes of the components used in the methods of the first and second aspects.

Further, the thickness and strength of the film correspond to the amount of pressure placed on the top plate and the amount of plasma applied. Films prepared in a 4"×4" mold pressurized for 30 to 120 seconds with 700 pounds force, i.e. about 44 psi or 300 kPa, have a thickness of about 0.02 mm when prepared from 30 ml of clotting mixture (such films are referred to as "SUBC 30" below). Films prepared correspondingly but from 60 ml clotting mixture have a thickness of about 0.03 mm (such films are referred to as "SUBC 60" below) and films prepared correspondingly but from 120 ml clotting mixture have a thickness of 0.05-0.06 mm (such films are referred to as "SUBC 120" below).

As already described above, the films of the present invention, i.e. the films prepared by the methods of the first and second aspects are characterized by an advantageous flexibility and, therefore, by: a fold number of at least 1, such as at least 2, such as at least 3, such as at least 4, such as at least 5; a fold endurance of at least 10, such as at least 20, such as at least 30, such as at least 40, such as at least 50, such as at least 60, such as at least 70, such is at least 80, such as at least 90, such is at least 100; and/or a burst pressure of about 50 to 1000 mm Hg, or of about 100 to 1000 mm Hg, or of about 100 to 800 mm Hg, or of about 100 to 600 mm Hg, or of about 100 to 500 mm Hg, or of about 100 to 450 mm Hg, or of about 140 mm Hg, or of about 150 mm Hg, or of about 175 mm Hg, or of about 200 mm Hg, or of about 225 mm Hg, or of about 250 mm Hg, or of about 275 mm Hg, or of about 300 mm Hg, or of about 325 mm Hg, or of about 350 mm Hg, or of about 375 mm Hg, or of about 400 mm Hg.

In a further preferred embodiment the flexible plasma-based films are characterized by a reduced burst pressure after having been soaked in an aqueous solution containing 10% glycerol for 10 minutes. In particular, such soaked films are characterized by a burst pressure of 75% to 80% of that of a corresponding "dry" film, i.e. a film having a residual water content of about 4% and having the same thickness when dry.

In a further preferred embodiment, the flexible plasma-based film is characterized by a ratio of burst pressure/film thickness of 5000 to 9000 mm Hg/mm film thickness when dry (i.e. when having a residual water content of about 4%) and having a film thickness of 0.05-0.06 mm, or by a ratio of burst pressure/film thickness of 6000 to 7500 mm Hg/mm film thickness when dry (i.e. when having a residual water content of about 4%) and having a film thickness of 0.03 mm.

Accordingly and as already indicated above, the flexible plasma-based films of the present invention are prepared by the methods of the first and second aspects. Notwithstanding, the flexible plasma-based films of the present invention may also be characterized by their specific features already outlined above.

As such, in a fourth aspect the present invention relates to a flexible plasma-based film comprising between 0.1 to 10 IU of thrombin per ml of plasma and having a thickness ranging from about 0.005 to 0.1 mm, wherein the flexible film is characterized by a fold number of at least 1, such as at least 2, such as at least 4, such as at least 5. Preferably, the flexible plasma-based film is characterized by a fold endurance of at least 10, such as at least 20, such as at least 30, such as at least 40, such as at least 50, such as at least 60, such as at least 70, such is at least 80, such as at least 90, such is at least 100, and/or by a burst pressure of about 50 to 1000 mm Hg, or of about 100 to 1000 mm Hg, or of about 100 to 800 mm Hg, or of about 100 to 600 mm Hg, or of about 100 to 500 mm Hg, or of about 100 to 450 mm Hg, or of about 140 mm Hg, or of about 150 mm Hg, or of about 175 mm Hg, or of about 200 mm Hg, or of about 225 mm Hg, or of about 250 mm Hg, or of about 275 mm Hg, or of about 300 mm Hg, or of about 325 mm Hg, or of about 350 mm Hg, or of about 375 mm Hg, or of about 400 mm Hg.

In particular, the flexible plasma-based films of the present invention are suitable for use as a hemostat, preferably as a hemostat to stop a mild to severe bleeding, and/or to stop an arterial bleeding. Preferably the films are also suitable: for use as an anti-adhesive sheet to reduce or prevent development of a surgery-induced adhesion; for use as a wound healing patch; for use as a wound dressing; or for use in hernia repair.

EXAMPLES

The invention is further described by the following non-limiting Examples.
SUBC Films
SUBC 30
A highly flexible plasma based film was prepared by mixing 30 ml plasma with either 280-320 µl thrombin (300 IU/ml) or 280-320 µl calcium solution (2 M $Ca^{2+}$) or 280-320 µl thrombin (300 IU/ml) together with about 280-320 µl calcium solution (2 M $Ca^{2+}$), subsequently incubating the mixture at 25-37° C. for about 15 minutes, in a 4"×4" mold and pressurizing the obtained plasma clot in the mold with a pressure of about 44 psi for about 60 seconds.

Finally, the obtained film was dried in a laminar hood overnight to a residual moisture content of about 4%. This film is indicated in Tables 3 and 4 below as "SUBC 30 (dry)".
SUBC 60
A highly flexible plasma based film was prepared by mixing 60 ml plasma with either 580-620 µl thrombin (300 IU/ml) or 580-620 µl calcium solution (2 M $Ca^{2+}$) or 580-620 µl thrombin (300 IU/ml) together with about 580-620 µl calcium solution (2 M $Ca^{2+}$), subsequently incubating the mixture at 25-37° C. for about 15 minutes, in a 4"×4" mold and pressurizing the obtained plasma clot in the mold with a pressure of about 44 psi for about 60 seconds.

Finally, the obtained film was dried in a laminar hood overnight to a residual moisture content of about 4%. This film is indicated in Tables 3 and 4 below as "SUBC 60 (dry)".

Some of the SUBC 60 (dry) films were subsequently soaked in 10% glycerol for 10 minutes. Such films are indicated as "SU BC 60 (soaked)".
SUBC 120
A highly flexible plasma based film was prepared by mixing 120 ml plasma with either 1180-1220 µl thrombin (300 IU/ml) or 1180-1220 µl calcium solution (2 M $Ca^{2+}$) or 1180-1220 µl thrombin (300 IU/ml) together with about 1180-1220 µl calcium solution (2 M $Ca^{2+}$), subsequently incubating the mixture at 25-37° C. for about 15 minutes, in a 4"×4" mold and pressurizing the obtained plasma clot in the mold with a pressure of about 44 psi for about 60 seconds.

Finally, the obtained film was dried in a laminar hood overnight to a residual moisture content of about 4%. This film is indicated in Tables 3 and 4 below as "SUBC 120 (dry)".

Some of the SUBC 120 (dry) films were subsequently soaked in 10% glycerol for 10 minutes-. Such films are indicated as "SUBC 120 (soaked)".
CE Films Comparative Example 1—CE-1

One prior-art blood plasma based film is known from EP 0485210 A2. Production method "4. Plasma Membrane" teaches mixing of 50 ml citrated plasma with 8-10 NIH units thrombin in a mold apparatus at 4° C. and warming to room temperature or 37° C. Obtained films might eventually be dried overnight in a laminar flow hood, compressed or desiccated. In order to get most comparable results the mixture was up-scaled to 60 ml. In particular 60 ml of plasma were mixed with 12 NIH units of thrombin. The mixture was warmed to 37° C. in a 4"×4" mold and was kept for 2 hour at this temperature. Finally the films were compressed with 44 psi for 60 seconds, excess water and serum was removed and the films were dried overnight under a laminar flow hood.

Thus prepared films are indicated in tables 1 and 2 as "CE-1 60 (dry)" and films that were additionally soaked in 10% glycerol for 10 minutes are indicated as "CE-1 60 (soaked)".

Comparative Example 2—CE-2

U.S. Pat. No. 8,529,959 B2 discloses a sheet comprising a blood plasma-derived plastic, which is pliant, elastic or a combination thereof.

The source material (a powder of clotted plasma) was obtained as described in Example 11 by clotting of 52.6 parts plasma by addition of 1 part 1M calcium chloride in water and lyophilization of the clot for 72 hours at a reduced pressure of 6 mTorr. Plasma powder was achieved by grinding the dried material in a mechanical grinder then sieving through a 150 µm sieve. Further procedures to formulate and form the plasma-derived plastic were the following. To formulate the plastic, 650 mg of plasma powder and 350 mg of glycerol (as plasticizer) were added to a small beaker. The components were mixed until homogeneous and allowed to incubate at room temperature in a closed container for approximately 21 hours. The resulting "dough" was molded in a press at 59° C. An actual description of forming a sheet or film is not given, but U.S. Pat. No. 8,529,959 B2 refers to U.S. patent application Ser. No. 11/495,115 (U.S. Ser. No. 11/495,115) to process elastic sheets.

Said patent application unfortunately only contains information about production of fibrinogen and gelatin based films. By combination of teachings disclosed in Examples 24, 16, 2 and 1 the common process of mixing a powder (ground fibrin, ground plasma clot, ground gelatin or non-polymerized fibrinogen) with various amounts of a plasticizer (glycerol) to produce a "dough" and forming the dough in a heated press was deducible. It was also indicated that films prepared from a dough containing 12.5% glycerol were most flexible and that films could be made at any pressure with 1000 to 8000 lbs.

It was thus decided to undertake experiments with non-polymerized fibrinogen and a plasma clot powder prepared as taught in U.S. Pat. No. 8,529,959 B2, admixing 12.5% of glycerol as taught in U.S. Ser. No. 11/495,115 or 35% as taught in U.S. Pat. No. 8,529,959 B2 and finalize the production process by pressure molding in a down-scaled 2"×1.6" mold at 59° C. and 5000 pounds. Initial experiments with doughs containing 35% glycerol revealed that obtained films were quite rigid, hardly flexible and it was not possible to achieve a single fold with such a film. Films prepared with 12.5% glycerol were to some extent flexible and this approach was examined further. Films prepared with 12.5% water, which is also mentioned in the patent (application) as plasticizer, but no glycerol revealed practically no cohesion.

Based on the initial experience of rather poor film properties it was decided to produce films comparable in plasma content to 120 ml films of the present invention. In order to get most comparable results a portion, being equivalent to the area of the 4"×4" mold divided by the area of the down-scaled mold, of 120 ml plasma was clotted and lyophilized as taught in U.S. Pat. No. 8,529,959 B2. The weight of this clot, i.e. 88-92 mg, in particular about 90 mg, had been determined and served as the weight of powderized plasma clot to be used for the experiments resembling a 120 ml film. The films were to some degree pliable, flexible and almost managed to survive one folding in the fold number test, but finally they failed to reach a fold number of 1. It was possible to determine burst pressure, but the results of dry films were so poor that they were not tested as soaked films. Comparative films resembling a 120 ml film are indicated in tables 1 and 2 as "CE-2 120 (dry)".

Comparative Example 3 (CE-3)

CE-3 is a commercially available anti-adhesion film used in the anti-adhesion animal study.

Comparative Example 4 (CE-4)

CE-4 is a commercially available anti-adhesion film used in the anti-adhesion animal study.

Anti-Adhesive Films 1 to 4
Film 1

Initially a film in accordance with the preparation of the SUBC 120 (dry) film described above was prepared.

Subsequently the film was soaked in an anti-adhesive agent solution prior to use. In particular, the SUBC 120 (dry) film was soaked in 7.5 ml of a solution consisting of 0.5 ml Tween-80®, 0.25 ml glycerin, 15 mg heparin, and 6.75 ml water. Thus soaked Tween-80® films were used in an anti-adhesion animal study and the results are given in Table 2 indicated as "Film 1".

Film 2

Initially a film in accordance with the preparation of the SUBC 120 (dry) film described above was prepared.

However, during preparation of the SUBC 120 (dry) film 1-2% of an anti-adhesive agent, such as Pluronic F68®, was admixed with the plasma. This film can either be used as dry film or as a soaked film after soaking. Soaking of a Pluronic F68® containing 120 ml plasma film in 7.5 ml of a solution consisting of 0.75 ml glycerin, 15 mg heparin, and 6.75 ml water provided a good anti-adhesion barrier.

Thus soaked pluronic films were used in an anti-adhesion animal study and the results are given in Table 2 indicated as "Film 2".

Film 3

Initially a film in accordance with the preparation of the SUBC 120 (dry) film described above was prepared.

However, during preparation of the SUBC 120 (dry) film 1-2% of two anti-adhesive agents at equal weight were admixed with the plasma. Namely, equal amounts of Tween-80® and Pluronic F68® by weight were admixed with the plasma Such films were used in an anti-adhesion animal study and the results are given in Table 2 indicated as "Film 3".

Film 4

Initially a film in accordance with the preparation of the SUBC 120 (dry) film described above was prepared.

Subsequently, anti-adhesive agents were topically applied to the film. Namely, a COX-2 inhibitor, such as Nimesulide® was applied in 1 mg/cm$^2$ by spray-drying, and the film was used as a dry film.

Such films with Nimesulide® being topically applied in 1 mg/cm$^2$ were used in an anti-adhesion animal study and the results are given in Table 2 indicated as "Film 4".

Example 1

Hemostatic Films—Animal Study for Determination of Efficacy.

Highly flexible plasma-based films for use as hemostats in accordance with the preparation of the SUBC 120 (dry) film described above were prepared.

The films were then subsequently modified by topical application for fast hemostasis with thrombin. Similar films were also prepared with fibrinogen being spray dried on one side of a film, followed by covering the fibrinogen with a layer of starch and finally spray-drying thrombin on top of the starch.

Efficacy of hemostatic films was evaluated in a porcine animal model by inducing a spleen, kidney or liver injury using a template bleeding device, which created a shallow wound of approximately 1 cm in diameter.

Evaluation of efficacy was performed after manually pressing the film on the wound for 3 minutes and waiting for 15 minutes thereafter without pressing. The flexible plasma-based films of the present invention tested had a hemostatic pharmaceutically-active agent topically applied. Namely, hemostats comprising topically applied thrombin, activated coagulation factor VII (FVIIa) or a combination of thrombin and fibrinogen were tested.

Hemostatic films with thrombin or a combination of thrombin and fibrinogen were most effective and stopped bleedings within 3 minutes. Films with FVIIa were slightly less effective as a particularly strong arterial bleeding could not be completely stopped by one FVIIa film after several minutes, in order to stop this bleeding a thrombin coated film of the present invention, which stopped this arterial bleeding, was finally used.

Example 2

Anti-Adhesive Sheets—Animal Study for Determination of Efficacy.

Efficacy of anti-adhesive sheets according to the present invention was evaluated in a rat animal model. In each animal, standardized surgical injuries (2.0×2.5 cm area) were applied to both the right and left sidewall peritoneum and uterine horns using a cytobrush until punctuate bleeding occurred.

The assigned test or control sheets were applied to cover the abrasion on each uterine horn and sutured into place. Control films were commercially available implants with dedicated anti-adhesive function. At day 7 following surgery, all animals were humanely euthanized and subjected to necropsy for gross assessment of adhesions.

Quality and Quantity of Adhesions were Evaluated as Follows:

Quantity: The quantity was scored according to the incidence of traumatized areas with adhesions and the adhesion coverage (which is calculated as a fraction of adhesions and translated into a percentage of traumatized area).

Quality: The quality of the induced adhesions was scored in accordance with Table 1. The results of quality and quantity are presented in Table 2. Adhesion quality was considered "filmy" if the scale of a ruler was visible through the tissue, and otherwise considered "dense."

TABLE 1

(Scoring of Adhesion Quality)

| Score | Description |
|---|---|
| 0 | No adhesion |
| 1 | A vascular adhesion |
| 2 | Filmy vascular adhesion |
| 3 | Dense, vascular adhesion, uterine horn not visible due to adhesiogenesis |

TABLE 2

(Quality and Quantity of anti-adhesion results)

| Anti-adhesion film | Quality | Quantity [% Surface area Covered with Adhesions] |
|---|---|---|
| Film 1 | 0 | 0 |
| Film 2 | 1 | 10-15 |
| Film 3 | 0-1 | 0-15 |
| Film 4 | 0-1 | 0-10 |
| CE-3 | 2-3 | 70-100 |
| CE-4 | 2 | 40 |

Films 1-4 of the present invention performed remarkably better than commercially available anti-adhesion films.

Example 3

Assessment of Film Flexibility.

The flexibility of the plasma-based films of the present invention, namely for films SUBC 30 (dry), SUBC 60 (dry) and (soaked), SUBC 120 (dry) and (soaked) and for the comparative films CE-1 60 (dry) and (soaked) and CE-2 120 (dry) was assessed by determining the fold number, fold endurance and burst pressures as described above.

Results

TABLE 3

(Fold Number, Fold Endurance)

| Film - ml | Fold Nr. | Fold Endurance |
|---|---|---|
| SUBC 30 (dry) | 5 | 100 |
| SUBC 60 (dry) | 5 | 100 |
| SUBC 60 (soaked) | 5 | 100 |
| SUBC 120 (dry) | 5 | 100 |
| SUBC 120 (soaked) | 5 | 100 |
| CE-1 60 (dry) | 0 | 0 |
| CE-1 60 (soaked) | 0 | 0 |
| CE-2 120 (dry) | 0 | 0 |

As none of comparative films CE-1 and CE-2 managed to achieve a single fold without breaking it was not possible to determine fold endurance.

TABLE 4

(Burst Pressure)

| Film - ml | Thickness [mm] | Burst Pressure [mmHg] | average Burst Pr. [mm Hg] | Burst Pr./mm Thickness |
|---|---|---|---|---|
| SUBC 30 (dry) | 0.02 | | | |
| SUBC 60 (dry) | 0.03 | 186-218 | 198 | 6200-7267 |

TABLE 4-continued (Burst Pressure)

| Film - ml | Thickness [mm] | Burst Pressure [mmHg] | average Burst Pr. [mm Hg] | Burst Pr./mm Thickness |
|---|---|---|---|---|
| SUBC 60 (soaked) | | 149-162 | 156 | |
| SUBC 120 (dry) | 0.05-0.06 | 318-441 | 404 | 5300-8820 |
| SUBC 120 (soaked) | | 194-400 | 314 | |
| CE-1 60 (dry) | | 0 | | |
| CE-1 60 (soaked) | | 10-33 | | |
| CE-2 120 (dry) | | 20-25 | | |

CE-1 (dry) films were so brittle and inflexible that they could not be placed in the fixture without breaking them. It was thus not possible to determine burst pressure for these films.

Many modifications and other embodiments of the invention set forth herein will come to mind to the one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

LIST OF REFERENCE SIGNS 1 plasma-based film
2 pharmaceutically-active agent
3 further pharmaceutically-active agent-spray-dried plasma
4 further pharmaceutically-active agent-spray-dried activator of the coagulation system
5 clotting mixture
6 solid, non-porous plate
7 mold
8 liquid removal system, such as vacuum-driven suction
9 downward piston
10 absorbent material

What is claimed is:

1. A flexible plasma-based film comprising between 2.5 and 10 International Units (IU) of thrombin per ml of undiluted plasma and having a thickness ranging from about 0.005 to 0.1 mm, wherein said flexible film is characterized by a burst pressure of about 50 to 1000 mm Hg obtainable by subjecting the film to a pressure of up to 125 psi in a mold.

2. The flexible plasma-based film according to claim 1, wherein said flexible film is characterized by a burst pressure of about 100 to 1000 mm Hg.

3. The flexible plasma-based film according to claim 1, wherein said flexible film is characterized by a water content of about 3 to 6% by weight.

4. The flexible plasma-based film according to claim 1, wherein said flexible film comprises at least one pharmaceutically-active agent.

5. The flexible plasma-based film according to claim 1, wherein said flexible film comprises at least one pharmaceutically-active agent homogeneously distributed throughout said film.

6. The flexible plasma-based film according to claim 4, wherein the at least one pharmaceutically-active agent is selected from the group consisting of: antibiotic agents; anti-inflammatory agents; anti-infective agents; growth factors; chemokines; immunomodulators; wound healing agents; activators of the coagulation system; anti-coagulation agents; anti-adhesion agents; anti-fibrinolytic agents; penicillin; silver; chlorhexidine; stromal cell-derived chemokines; stromal cell-derived factor 1 alpha; stromal cell-derived factor 1 beta; fibrinogen; Factor VIIa; CXCL-12; heparin; aprotinin; tranexamic acid; non-ionic surfactants; polyoxyethylene-polyoxypropylene block copolymer; polysorbate 80; COX-2 inhibitors; and Nimesulide.

7. The flexible plasma-based film according to claim 5, wherein the at least one pharmaceutically-active agent is selected from the group consisting of: antibiotic agents; anti-inflammatory agents; anti-infective agents; growth factors; chemokines; immunomodulators; wound healing agents; activators of the coagulation system; anti-coagulation agents; anti-adhesion agents; anti-fibrinolytic agents; penicillin; silver; chlorhexidine; stromal cell-derived chemokines; stromal cell-derived factor 1 alpha; stromal cell-derived factor 1 beta; fibrinogen; Factor VIIa; CXCL-12; heparin; aprotinin; tranexamic acid; non-ionic surfactants; polyoxyethylene-polyoxypropylene block copolymer; polysorbate 80; COX-2 inhibitors; and Nimesulide.

8. The flexible plasma-based film according to claim 1, wherein said plasma is animal or human blood plasma.

9. The flexible plasma-based film according to claim 1, wherein said plasma is Fresh Frozen Plasma (FFP) or is pathogen-safe plasma.

10. The flexible plasma-based film according to claim 1, wherein said film comprises one or more humectants.

11. The flexible plasma-based film according to claim 1, wherein said film comprises an adhesive backing.

12. The flexible plasma-based film according to claim 1, wherein said film is a sterilized film.

13. The flexible plasma-based film according to claim 1, wherein said film is packaged in a humidity-controlled container.

14. The flexible plasma-based film according to claim 1, wherein said flexible film is characterized by a burst pressure of about 100 to 800 mm Hg.

15. The flexible plasma-based film according to claim 1, wherein said flexible film is characterized by a burst pressure of about 100 to 600 mm Hg.

* * * * *